(12) United States Patent
Yao

(10) Patent No.: US 9,452,260 B2
(45) Date of Patent: Sep. 27, 2016

(54) CLOSED LOOP CONTROL SYSTEM BASED ON A NON-INVASIVE CONTINUOUS SENSOR

(71) Applicant: Verily Life Sciences LLC, Mountain View, CA (US)

(72) Inventor: Huanfen Yao, Sunnyvale, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 157 days.

(21) Appl. No.: 14/088,280

(22) Filed: Nov. 22, 2013

(65) Prior Publication Data

US 2015/0148774 A1 May 28, 2015

(51) Int. Cl.
| | |
|---|---|
| *A61M 5/172* | (2006.01) |
| *A61B 5/145* | (2006.01) |
| *G02C 7/04* | (2006.01) |
| *A61M 5/142* | (2006.01) |
| *A61B 5/00* | (2006.01) |
| *A61B 10/00* | (2006.01) |

(52) U.S. Cl.
CPC ........ *A61M 5/1723* (2013.01); *A61B 5/14507* (2013.01); *A61B 5/14532* (2013.01); *A61B 5/4836* (2013.01); *A61B 5/6821* (2013.01); *A61M 5/14244* (2013.01); *G02C 7/04* (2013.01); *A61B 2010/0067* (2013.01); *A61M 2205/3317* (2013.01); *A61M 2205/3561* (2013.01); *A61M 2205/3584* (2013.01); *A61M 2205/3592* (2013.01); *A61M 2205/6054* (2013.01); *A61M 2210/0612* (2013.01); *A61M 2230/005* (2013.01); *A61M 2230/201* (2013.01)

(58) Field of Classification Search
CPC ............ A61M 2205/3317; A61M 2205/3561; A61M 2205/3584; A61M 2205/3592; A61M 2205/6054; A61M 2210/0612; A61M 2230/005; A61M 5/1723; A61B 5/00; A61B 5/0002; A61B 5/14532; A61B 2010/0067; A61B 5/14507; A61B 5/4836; A61B 5/6821
See application file for complete search history.

(56) References Cited

U.S. PATENT DOCUMENTS

| | | | |
|---|---|---|---|
| 3,958,560 A * | 5/1976 | March | 600/319 |
| 6,936,007 B2 | 8/2005 | Quy | |
| 6,980,842 B2 | 12/2005 | March et al. | |
| 7,156,808 B2 | 1/2007 | Quy | |
| 7,988,630 B1 | 8/2011 | Osorio et al. | |
| 8,277,377 B2 | 10/2012 | Quy | |
| 8,348,842 B1 * | 1/2013 | Osorio | A61B 5/14528 600/345 |

(Continued)

OTHER PUBLICATIONS

International Search Repoert issued in connection with co-pending International Applicaiton No. PCT/US2014/062782, ISA/KR, dated Jan. 30, 2015.

(Continued)

*Primary Examiner* — Quynh-Nhu H Vu
(74) *Attorney, Agent, or Firm* — McDonnell Boehnen Hulbert & Berghoff LLP

(57) ABSTRACT

Methods and systems for controlling analyte levels are described. An example method may include receiving a sensor measurement relating to an eye-mountable device. The method also may include determining an analyte concentration based on the one or more sensor measurements, and comparing the analyte concentration to a target analyte concentration. Based on the comparing, the method further may include providing instructions to a drug delivery device, where the instructions are configured to control a drug delivery rate by the drug delivery device.

6 Claims, 9 Drawing Sheets

(56) References Cited

U.S. PATENT DOCUMENTS

| | | | |
|---|---|---|---|
| 8,385,998 B2* | 2/2013 | Zhang | A61B 5/14532 600/318 |
| 8,452,361 B2 | 5/2013 | Muller | |
| 2006/0183986 A1 | 8/2006 | Rice et al. | |
| 2007/0016127 A1* | 1/2007 | Staib | A61B 5/14532 604/66 |
| 2009/0076367 A1* | 3/2009 | Sit | A61B 3/16 600/398 |
| 2009/0221890 A1* | 9/2009 | Saffer | A61B 5/14532 600/347 |
| 2010/0113901 A1 | 5/2010 | Zhang et al. | |
| 2010/0185066 A1* | 7/2010 | March | A61B 5/1455 600/319 |
| 2011/0040161 A1 | 2/2011 | Abreu | |
| 2011/0208155 A1* | 8/2011 | Palerm | G06F 19/3456 604/503 |
| 2011/0313390 A1 | 12/2011 | Roy et al. | |
| 2012/0245444 A1* | 9/2012 | Otis et al. | 600/345 |
| 2013/0053818 A1 | 2/2013 | Estes | |
| 2013/0053819 A1* | 2/2013 | Estes | A61M 5/14244 604/504 |
| 2013/0090534 A1* | 4/2013 | Burns | A61B 3/16 600/301 |
| 2014/0005501 A1* | 1/2014 | Schabbach | A61B 5/14532 600/301 |
| 2014/0275923 A1* | 9/2014 | Haffner | A61B 5/6867 600/377 |

OTHER PUBLICATIONS

Written Opinion issued in connection with co-pending International Application No. PCT/US2014/062782, ISA/KR, dated Jan. 30, 2015.

Yu-Te Liao, "A 3-µW CMOS Glucose Sensor for Wireless Contact-Lens Tear Glucose Monitoring," IEEE Journal of Solid-State Circuits, vol. 47, No. 1, pp. 335-344 (2012).

* cited by examiner

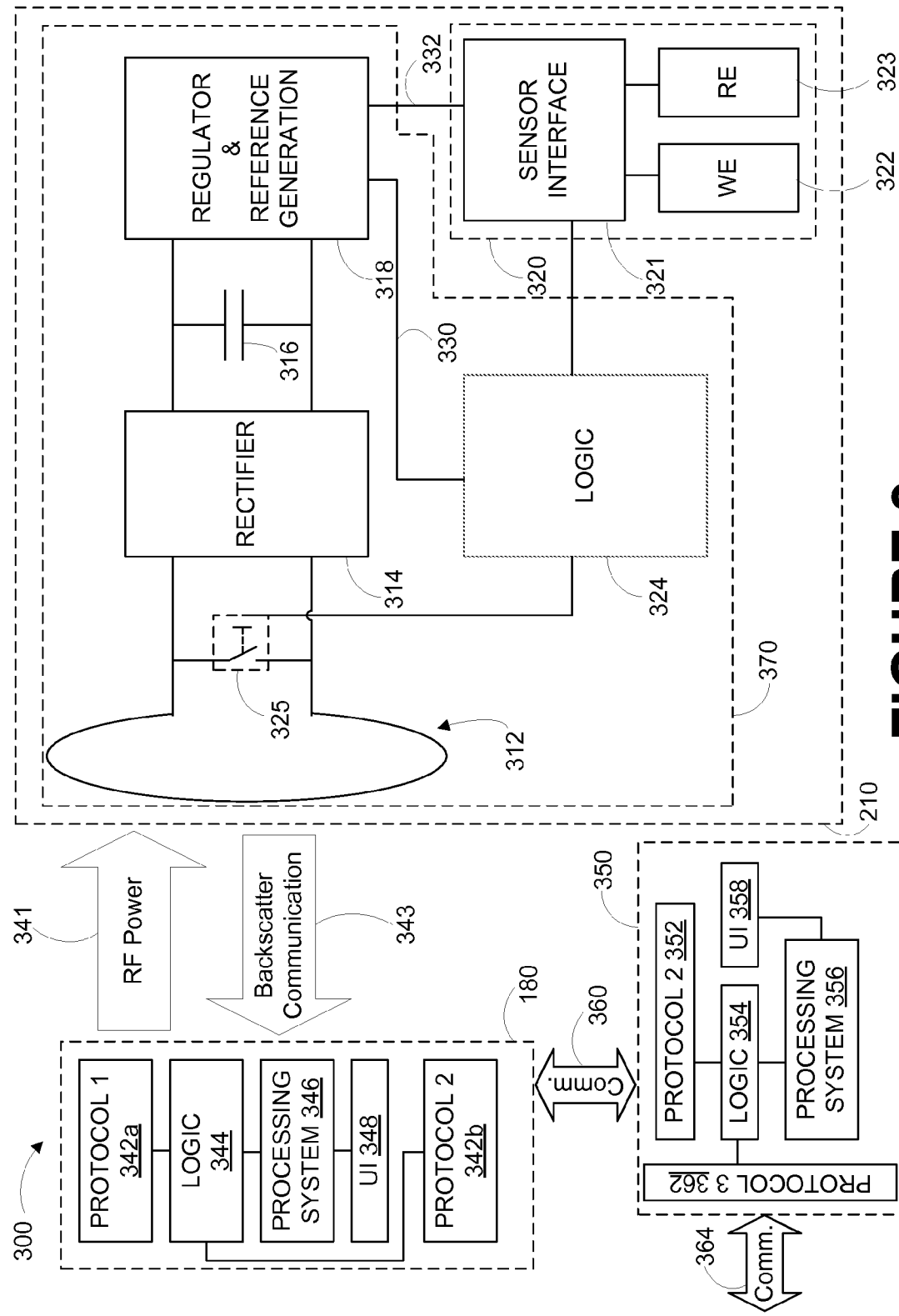

US 9,452,260 B2

CLOSED LOOP CONTROL SYSTEM BASED ON A NON-INVASIVE CONTINUOUS SENSOR

BACKGROUND

Diabetes is a group of metabolic diseases in which a person has high blood sugar, either because the pancreas does not produce enough insulin, or because cells do not respond to the insulin that is produced. Diabetes is widely recognized as a leading cause of death and disability throughout the world, and the number of people diagnosed with diabetes mellitus is expected to increase dramatically in the next few decades. Diabetes management can involve changes in diet and/or use of insulin to maintain normal blood sugar levels.

SUMMARY

The present disclosure describes embodiments that relate to a closed loop control of analyte levels. In one aspect, the present application describes a method. The method includes receiving one or more sensor measurements relating to an eye-mountable device. The eye-mountable device includes a polymeric material having a concave surface and a convex surface opposite the concave surface. The concave surface is configured to be removably mounted over a corneal surface and the convex surface is configured to be compatible with eyelid motion when the concave surface is so mounted. The method also includes determining a glucose concentration based on the one or more sensor measurements. The method further includes obtaining a target glucose concentration. The method also includes comparing the glucose concentration to the target glucose concentration, and, based on the comparing, providing instructions to an insulin delivery device, where the instructions are configured to control an insulin delivery rate by the insulin delivery device.

In another aspect, the present disclosure describes a system. The system includes an eye-mountable device including a polymeric material having a concave surface and a convex surface opposite the concave surface. The concave surface is configured to be removably mounted over a corneal surface and the convex surface is configured to be compatible with eyelid motion when the concave surface is so mounted. The system also includes an electrochemical sensor mounted in the eye-mountable device and configured to provide one or more sensor measurements. The system further includes a reader including one or more antennas configured to: (i) transmit radio frequency (RF) radiation to power the eye-mountable device and the electrochemical sensor, and (ii) receive indications of the one or more sensor measurements. The system also includes a controller in communication with the reader. The controller is configured to: (i) receive information related to the one or more sensor measurements from the reader; (ii) determine a glucose concentration based on the information; (iii) obtain a target glucose concentration; (iv) compare the glucose concentration to the target glucose concentration; and (v) based on the comparing, provide instructions to an insulin delivery device to control an insulin delivery rate to a blood stream by the insulin delivery device.

In still another aspect, the present disclosure describes a non-transitory computer readable medium having stored thereon instructions that, when executed by a computing device, cause the computing device to perform functions. The functions include receiving information related to one or more sensor measurements indicative of a concentration of an analyte. The one or more sensor measurements are obtained by a sensor in an eye-mountable device. The eye-mountable device comprises a transparent polymeric material having a concave surface and a convex surface opposite the concave surface. The concave surface is configured to be removably mounted over a corneal surface and the convex surface is configured to be compatible with eyelid motion when the concave surface is so mounted. The functions also include determining the concentration of the analyte based on the information. The functions further include obtaining a target concentration for the analyte. The functions also include comparing the concentration of the analyte to the target concentration for the analyte, and, based on the comparing, providing instructions to a drug delivery device, where the instructions are configured to control a drug delivery rate by the drug delivery device.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE FIGURES

FIG. 3 is a functional block diagram of an example system for electrochemically measuring a tear-film analyte concentration, in accordance with an example embodiment.

DETAILED DESCRIPTION

Figure 1:
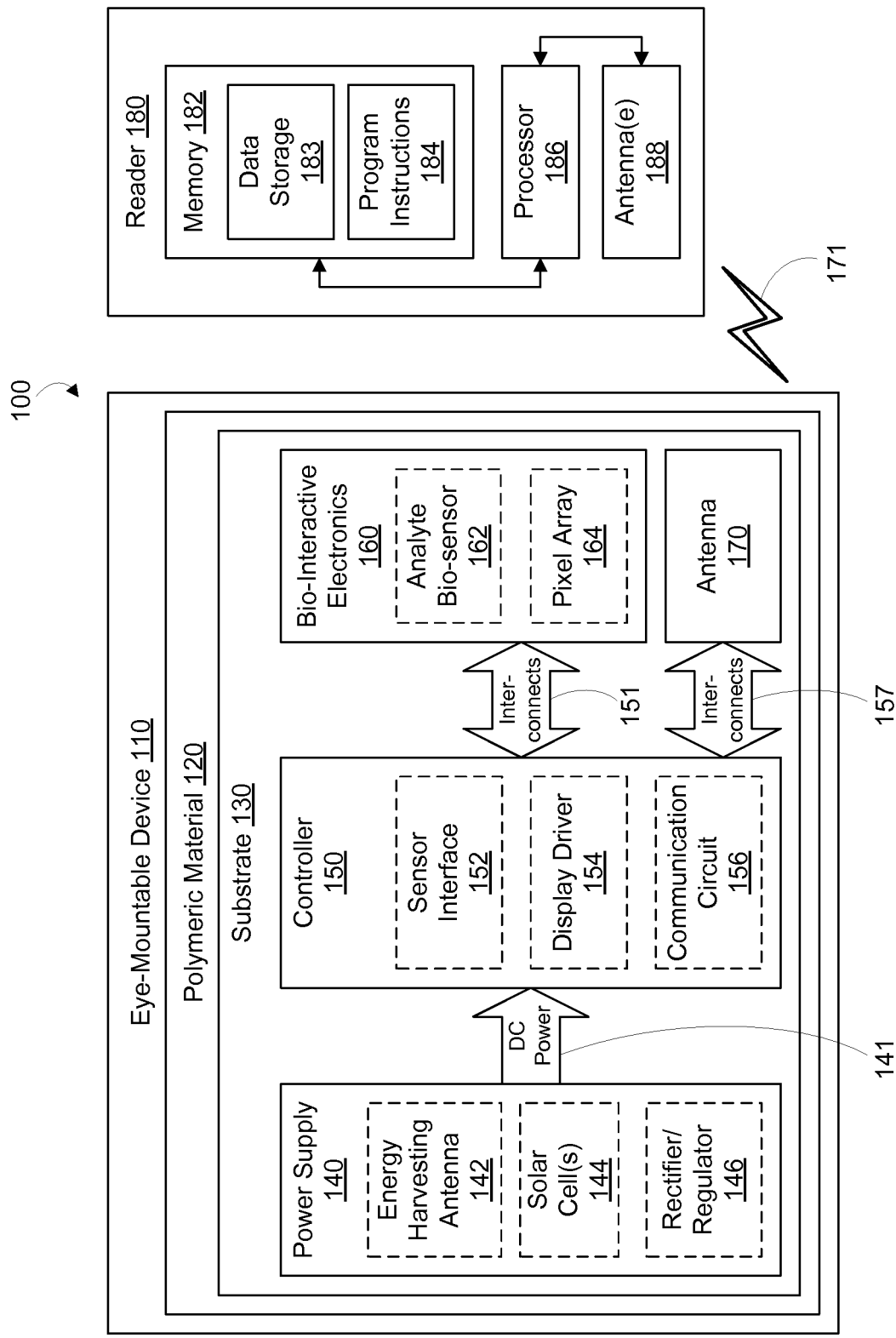
FIG. 1 is a block diagram of an example system that includes an eye-mountable device in wireless communication with a reader, in accordance with an example embodiment.

The following detailed description describes various features and functions of the disclosed systems and methods with reference to the accompanying figures. In the figures, similar symbols identify similar components, unless context dictates otherwise. The illustrative system and method embodiments described herein are not meant to be limiting. It may be readily understood that certain aspects of the disclosed systems and methods can be arranged and combined in a wide variety of different configurations, all of which are contemplated herein.

I. Overview

In an example, an ophthalmic sensing platform can include a sensor, control electronics, and an antenna all situated on a substrate embedded in a polymeric material. The polymeric material can be incorporated in an ophthalmic device, such as an eye-mountable device or an implantable medical device. The control electronics can operate the sensor to perform readings and can operate the antenna to wirelessly communicate the readings from the sensor to a reader via the antenna.

In some examples, the polymeric material can be in the form of a round lens with a concave curvature configured to mount to a corneal surface of an eye, such as a contact lens. The substrate can be embedded near the periphery of the polymeric material to avoid interference with incident light received closer to the central region of the cornea. The sensor can be arranged on the substrate to face inward, toward the corneal surface, so as to generate clinically relevant readings from near the surface of the cornea and/or from tear fluid interposed between the polymeric material and the corneal surface. Additionally or alternatively, the sensor can be arranged on the substrate to face outward, away from the corneal surface and toward the layer of tear fluid coating the surface of the polymeric material exposed to the atmosphere. In some examples, the sensor is entirely embedded within the polymeric material. For example, an electrochemical sensor that includes a working electrode and a reference electrode can be embedded in the polymeric material and situated such that the sensor electrodes are less than 10 micrometers from the polymeric surface configured to mount to the cornea. The sensor can generate an output signal indicative of a concentration of an analyte that diffuses through the lens material to the sensor electrodes.

Tear fluid contains a variety of inorganic electrolytes (e.g., $Ca^{2+}$, $Mg^{2+}$, $Cl^-$) and organic components (e.g., glucose, lactate, proteins, lipids, etc.) that can be used to diagnose health states. An ophthalmic sensing platform including the above-mentioned sensor can be configured to measure one or more of these analytes can thus provide a convenient non-invasive platform useful in diagnosing and/or monitoring health states. For example, an ophthalmic sensing platform can be configured to sense glucose and can be used by diabetic individuals to measure/monitor their glucose levels. In some examples, the sensor can be configured to measure additional or other conditions other than analyte levels; e.g., the sensor can be configured to measure light, temperature, pressure, etc.

In an example, an external reader device or "reader" can radiate radio frequency radiation to power the sensor. The reader may thereby control the operation of the sensing platform by controlling the supply of power to the sensing platform. In some examples, the reader can operate to intermittently interrogate the sensing platform to provide a reading by radiating sufficient radiation to power the sensing platform to obtain a measurement and communicate the result. The reader can also store the sensor results communicated by the sensing platform. In this manner, the reader can acquire for example, a series of analyte concentration measurements over time without continuously powering the sensing platform.

The sensor of the ophthalmic sensing platform can be configured with, or be part of, a Radio-frequency Identification (RFID) tag. The RFID tag and reader can communicate using an RFID protocol; e.g., an RFID Generation 2 protocol. The RFID tag can be configured to receive radio signals from the reader. In some examples, the reader's signals can be used for both communicating with and powering the RFID tag; while in other embodiments, the RFID tag can be a powered device; e.g., be configured with a battery that powers the tag.

The reader can communicate with other devices than the RFID tag. As one possible example, the reader can be equipped with a Bluetooth interface as well as with an RFID interface. The reader can communicate with other devices, e.g., a display device, via a Bluetooth or other protocol. In one example, the reader can obtain data from the RFID tag using RFID command(s); e.g., the RFID Generation 2 standard Read command. Upon obtaining the data, the reader can store, process, and/or communicate the data using the Bluetooth interface to another device, such as the display device. Other interfaces for communicating with devices using other communication protocol(s) are possible as well.

As an example, the above-mentioned eye-mountable device or contact lens can be configured with a sensor that includes an RFID tag. As mentioned above, the sensor can be configured to take measurements while being worn in an eye of a wearer. Upon taking the measurements, the sensor may store data related to the measurements, and subsequently send the data upon request from the reader. The reader, in turn, can store and/or process the received data. For example, the sensor can take current measurements of an analyte (e.g., glucose) in tear-film of the eye of the wearer and send data about the measured current(s) to the reader. The reader can process the current measurement data to determine analyte-related information about the wearer.

The tear-film analyte concentration information can be sent from the reader to a display device. The display device could be, for example, a wearable, laptop, desktop, handheld, or tablet computer, a mobile phone, or a subsystem of such a device. The display device can include a processing system; e.g., a central processing unit (CPU), and a non-transitory computer readable medium configured to store at least program instructions. One example of a wearable computer is a head-mountable display (HMD). The HMD can be a device that is capable of being worn on the head and places a display in front of one or both eyes of the wearer. The display device can store the data received from the reader, perhaps process the data, and generate display(s) based on the received and/or processed data. In some examples, the reader can be part of or integrated into the HMD.

In some examples, the reader and the display device can be configured with configuration data to perform glucose-related processing. For example, the reader can include configuration data such as current measurement data for various levels of glucose concentration. Based on this configuration data, the reader can determine a tear-film glucose concentration for the wearer. Also, the wearer can provide blood glucose concentration(s) and corresponding tear-film glucose concentration(s) for the wearer to the display device (for example, during configuration), and the display device can determine relationships between blood glucose concentration(s) and tear-film glucose concentration(s). The relationships between blood glucose concentration(s) and tear-film glucose concentration(s) can be obtained by other methods as well (e.g., the relationships may be predetermined and stored at the display device).

During operation of these examples, the RFID tag in an eye of the wearer can generate tear-film current data and send the tear-film current data to the reader. The reader can then process the tear-film current data to generate tear-film glucose concentration(s) and send the tear-film glucose concentration(s) to the display device. Then, the display device can be configured to receive tear-film glucose concentration(s) from the reader and generate corresponding blood glucose concentration(s). In some examples, either the reader or the display device can take tear-film current data as inputs and generate blood glucose concentration(s) as output(s); i.e., all processing can take place at either the reader or display device.

In some examples, the reader can be configured to be frequently worn in proximity to one or more contact lenses configured with sensors worn by a person. For example, the reader can be configured to be part of a pair of eyeglasses, jewelry (e.g., earrings, necklace), headband, head cover such as a hat or cap, earpiece, other clothing (e.g., a scarf), and/or other devices. As such, the reader can provide power and/or receive measurements while proximate to the worn contact lens(es).

Configuring the reader to be frequently worn in proximity to one or more contact lenses enables the lenses to have a reliable external power source and/or storage for sensor data collection, processing of sensor data, and transmission of unprocessed and/or processed sensor data to additional devices; e.g., the above-mentioned display device. Thus, the herein-described reader can provide valuable support functionality, including but not limited to power, communication, and processing resources, to enhance use of contact lenses with embedded sensors, while enabling consequent reduction of support functions on the contact lens. This reduction of support functions on the contact lens may free resources on the contact lens to enable addition of more and/or different sensors and to provide for other functionality on the contact lens.

In some examples, the display device may include a controller. The controller may be configured to obtain a target glucose concentration for the wearer or a patient wearing the eye-mountable device. The controller also may be configured to receive or establish, based on patient-specific information, a range about the target glucose concentration that is considered healthy or safe for the patient. Further, the controller may be configured to control an insulin delivery device (e.g., an insulin pump) configured to inject insulin into the wearer at a particular rate. The controller may be configured to control the insulin delivery device to maintain a predetermined insulin delivery rate while the blood glucose concentration is within the range or meets the target glucose concentration. The controller may be configured to control the insulin delivery device to apply a different insulin infusion rate if the patient's blood glucose concentration deviates outside of the range. In some examples, the controller may be configured to establish or estimate a rate of change in (i.e., a trajectory of) the glucose concentration over time and control the insulin delivery device further based on the established or estimate rate of change. Thus, the controller may be configured to control the insulin delivery device in a preemptive manner to control glucose concentration to be within a safe range over extended periods of time.

In examples, the controller could be separate or remote from the eye-mountable device and the display device. The controller may be, for example, a wearable, laptop, desktop, handheld, or tablet computer, a mobile phone, or a subsystem of such a device. The controller may be embedded in the reader or the insulin delivery device, for example. The controller may be in communication with the display device. The controller may be configured to provide glucose concentration information to the display device and generate a display of the information on the display device.

In an example, in addition or alternative to a glucose sensor configured to measure glucose concentration in a tear-film contacting the eye-mountable device, any other sensor or measuring mechanism can be used to measure glucose concentration. For instance, a light source may be configured to transmit light onto at least a portion of a retina of an eye of a user or patient. A sensor embedded in eye-mountable device may be configured to receive light from the retina. A reader or controller in communication with the sensor may be configured to determine blood glucose concentration of the user from the light received by the sensor. In another example, a device can capture images of the eye of the user and based on the image, the controller may be configured to determine glucose concentration. These are examples for illustration only, and any other measuring means can be used to provide information or measurements to the reader or the controller, which can be configured to determine the glucose concentration based on the information or the measurements.

Although the examples mentioned above are described in the context of measuring glucose concentration and controlling an insulin delivery device accordingly, the methods and systems described here can be used for controlling levels of any other analyte by controlling any drug delivery device. An example controller may be configured to receive information or sensor measurements relating to an eye-mountable device and indicative of concentration of an analyte. The controller may be configured to compare concentration of the analyte to a target analyte concentration. Based on the comparing, the controller may be configured to control a drug delivery device, where the instructions are configured to control a drug delivery rate by the drug delivery device so as to cause the concentration of the analyte to substantially meet the target analyte concentration.

II. Example Ophthalmic Electronics Platform

FIG. 1 is a block diagram of a system 100 that includes an eye-mountable device 110 in wireless communication with a reader 180. The exposed regions of the eye-mountable device 110 are made of a polymeric material 120 formed to be contact-mounted to a corneal surface of an eye. A substrate 130 is embedded in the polymeric material 120 to provide a mounting surface for a power supply 140, a controller 150, bio-interactive electronics 160, and a communication antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it is also referred to herein as an ophthalmic electronics platform.

To facilitate contact-mounting, the polymeric material 120 can have a concave surface configured to adhere ("mount") to a moistened corneal surface (e.g., by capillary forces with a tear-film coating the corneal surface). Additionally or alternatively, the eye-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some examples, the polymeric material 120 can be a deformable ("non-rigid") material to enhance wearer comfort. In some examples, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting to connection pads) and/or as a platform for patterning conductive materials (e.g., gold, platinum, palladium, titanium, copper, aluminum, silver, metals, other conductive materials, combinations of these, etc.) to create electrodes, interconnects, connection pads, antennae, etc. In some examples, substantially transparent conductive materials (e.g., indium tin oxide) can be patterned on the substrate 130 to form circuitry, electrodes, etc. For example, the antenna 170 can be formed by forming a pattern of gold or another conductive material on the substrate 130 by deposition, photolithography, electroplating, etc. Similarly, interconnects 151, 157 between the controller 150 and the bio-interactive electronics 160, and between the controller 150 and the antenna 170, respectively, can be formed by depositing suitable patterns of conductive materials on the substrate 130. A combination of microfabrication techniques including, without limitation, the use of photoresists, masks, deposition techniques, and/or plating techniques can be employed to pattern materials on the substrate 130. The substrate 130 can be a relatively rigid material, such as polyethylene terephthalate ("PET") or another material configured to structurally support the circuitry and/or chip-based electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some examples, the bio-interactive electronics 160 (and the substrate 130) can be positioned away from the center of the eye-mountable device 110 and thereby avoid interference with light transmission to the central, light-sensitive region of the eye. For example, where the eye-mountable device 110 is shaped as a concave-curved disk, the substrate 130 can be embedded around the periphery (e.g., near the outer circumference) of the disk. In some examples, however, the bio-interactive electronics 160 (and the substrate 130) can be positioned in or near the central region of the eye-mountable device 110. Additionally or alternatively, the bio-interactive electronics 160 and/or substrate 130 can be substantially transparent to incoming visible light to mitigate interference with light transmission to the eye. Moreover, in some examples, the bio-interactive electronics 160 can include a pixel array 164 that emits and/or transmits light to be received by the eye according to display instructions. Thus, the bio-interactive electronics 160 can optionally be positioned in the center of the eye-mountable device so as to generate perceivable visual cues to a wearer of the eye-mountable device 110, such as by displaying information (e.g., characters, symbols, flashing patterns, etc.) on the pixel array 164.

In examples, the substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius.

In examples, the power supply 140 may be configured to harvest ambient energy to power the controller 150 and the bio-interactive electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to/from the reader 180. That is, the functions of the communication antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such an analyte bio-sensor 162, in bio-interactive electronics 160 to obtain input from the biological environment. Additionally or alternatively, the interaction could involve the use of one or more components, such as pixel array 164, to provide an output to the biological environment.

In one example, the controller 150 includes a sensor interface module 152 that is configured to operate analyte bio-sensor 162. The analyte bio-sensor 162 can be, for example, an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction can generate an amperometric current that can be measured through the working electrode. The amperometric current can be dependent on the analyte concentration. Thus, the amount of the amperometric current that is measured through the working electrode can provide an indication of analyte concentration. In some examples, the sensor interface module 152 can be a potentiostat configured to apply a voltage difference between the working and reference electrodes of the amperometric electrochemical sensor while measuring a current through the working electrode.

In some instances, a reagent can also be included to sensitize the electrochemical sensor to one or more desired analytes. For example, a layer of glucose oxidase ("GOx") proximal to the working electrode can catalyze glucose oxidation to generate hydrogen peroxide ($H_2O_2$). The hydrogen peroxide can then be electro-oxidized at the working electrode, which releases electrons to the working electrode, resulting in an amperometric current that can be measured through the working electrode.

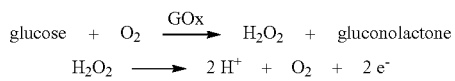

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current measured through the working electrode thus provides an indication of the analyte concentration.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivable by the reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical component. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided to components on a chip by rectifier and/or regulator components located on the same chip. That is, the functional blocks in FIG. 1 shown as the power supply block 140 and controller block 150 need not be implemented as physically separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

The reader 180 can be configured to be external to the eye; i.e., is not part of the eye-mountable device 110. Reader 180 can include one or more antennae 188 to send and receive wireless signals 171 to and from the eye-mountable device 110. In some examples, reader 180 can communicate using hardware and/or software operating according to one or more standards, such as, but not limited to, a RFID standard, a Bluetooth standard, a Wi-Fi standard, a Zigbee standard, etc.

Reader 180 can also include a computing system with a processor 186 in communication with a memory 182. Memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the analyte bio-sensor 162), program settings (e.g., to adjust behavior of the eye-mountable device 110 and/or reader 180), etc. The memory 182 can also include program instructions 184 for execution by the processor 186 to cause the reader 180 to perform processes specified by the instructions 184. For example, the program instructions 184 can cause reader 180 to provide a user interface that allows for retrieving information communicated from the eye-mountable device 110 (e.g., sensor outputs from the analyte bio-sensor 162). The reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

In some examples, reader 180 can be a smart phone, digital assistant, or other portable computing device with wireless connectivity sufficient to provide the wireless communication link 171. In other examples, reader 180 can be implemented as an antenna module that can be plugged in to a portable computing device; e.g., in scenarios where the communication link 171 operates at carrier frequencies not commonly employed in portable computing devices. In still other examples discussed below in more detail in the context of at least FIG. 5, the reader 180 can be a special-purpose device configured to be worn relatively near a wearer's eye to allow the wireless communication link 171 to operate with a low power budget. For example, the reader 180 can be integrated in eyeglasses, integrated in a piece of jewelry such as a necklace, earring, etc., integrated in an article of clothing worn near the head, such as a hat, headband, etc., or integrated in a head-mounted display device.

In an example where the eye-mountable device 110 includes an analyte bio-sensor 162, the system 100 can be operated to monitor the analyte concentration in tear-film on the surface of the eye. Thus, the eye-mountable device 110 can be configured as a platform for an ophthalmic analyte bio-sensor. The tear-film is an aqueous layer secreted from the lacrimal gland to coat the eye. The tear-film is in contact with the blood supply through capillaries in the structure of the eye and includes many biomarkers found in blood that are analyzed to characterize a person's health condition(s). For example, the tear-film includes glucose, calcium, sodium, cholesterol, potassium, other biomarkers, etc. The biomarker concentrations in the tear-film can be systematically different than the corresponding concentrations of the biomarkers in the blood, but a relationship between the two concentration levels can be established to map tear-film biomarker concentration values to blood concentration levels. For example, the tear-film concentration of glucose can be established (e.g., empirically determined) to be approximately one tenth the corresponding blood glucose concentration. However, any other ratio relationship and/or a non-ratio relationship may be used. Thus, measuring tear-film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 100 configured as a tear-film analyte monitor, the reader 180 can emit radio frequency radiation 171 that is harvested to power the eye-mountable device 110 via the power supply 140. Radio frequency electrical signals captured by the energy harvesting antenna 142 (and/or the communication antenna 170) are rectified and/or regulated in the rectifier/regulator 146 and a regulated DC supply voltage 141 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162. The applied voltage can be sufficient to cause the analyte to undergo an electrochemical reaction at the working electrode and thereby generate an amperometric current that can be measured through the working electrode. The measured amperometric current can provide the sensor reading ("result") indicative of the analyte concentration. The controller 150 can operate the antenna 170 to communicate the sensor reading back to the reader 180 (e.g., via the communication circuit 156). The sensor reading can be communicated by, for example, modulating an impedance of the communication antenna 170 such that the modulation in impedance is detected by the reader 180. The modulation in antenna impedance can be detected by, for example, backscatter radiation from the antenna 170.

In some examples, the system 100 can operate to non-continuously ("intermittently") supply energy to the eye-mountable device 110 to power the controller 150 and bio-interactive electronics 160. For example, radio frequency radiation 171 can be supplied to power the eye-mountable device 110 long enough to carry out a tear-film analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the reader 180 can accumulate a set of analyte concentration measurements over time without continuously powering the eye-mountable device 110.

Figure 2A:
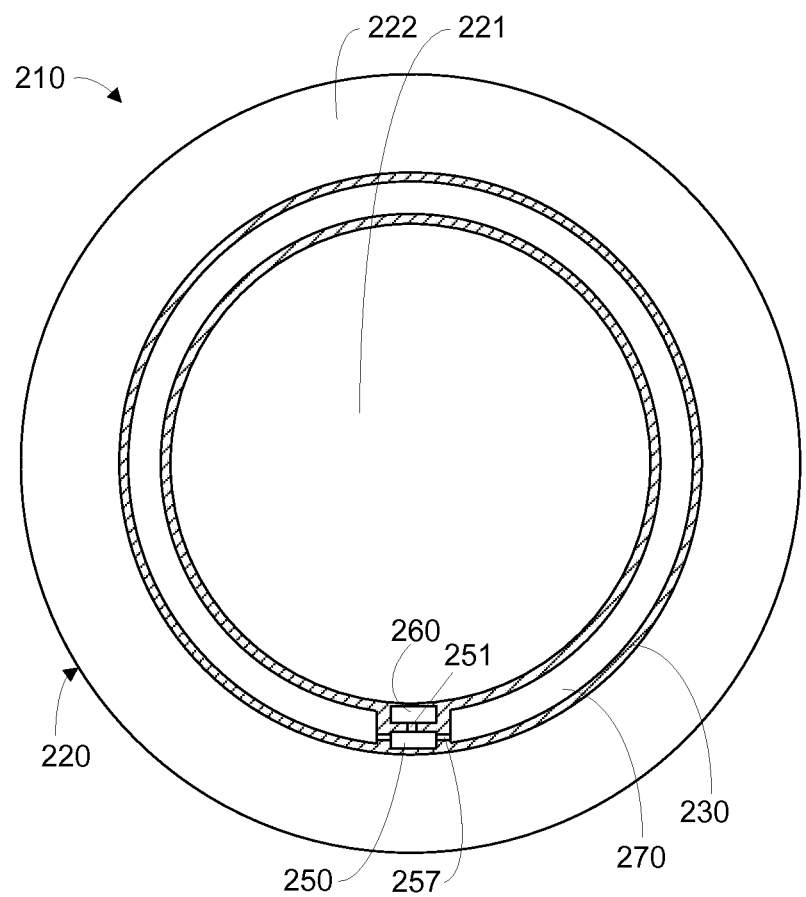
FIG. 2A is a bottom view of an example eye-mountable device, in accordance with an example embodiment.
Figure 2B:
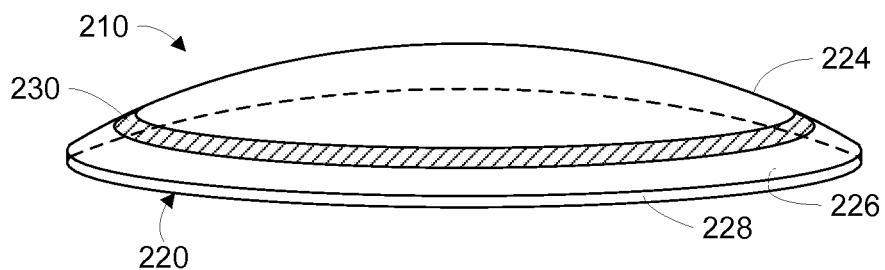
FIG. 2B is a side view of the example eye-mountable device shown in FIG. 2A, in accordance with an example embodiment.

FIG. 2A is a bottom view of an example eye-mountable electronic device 210 (or ophthalmic electronics platform), in accordance with an example embodiment. FIG. 2B is an aspect view of the example eye-mountable electronic device shown in FIG. 2A, in accordance with an example embodiment. It is noted that relative dimensions in FIGS. 2A and 2B are not necessarily to scale, but have been rendered for purposes of explanation only in describing the arrangement of the example eye-mountable electronic device 210. The eye-mountable device 210 is formed of a polymeric material 220 shaped as a curved disk. In some examples, eye-mountable device 210 can include some or all of the above-mentioned aspects of eye-mountable device 110. In other embodiments, eye-mountable device 110 can further include some or all of the herein-mentioned aspects of eye-mountable device 210.

The polymeric material 220 can be a substantially transparent material to allow incident light to be transmitted to the eye while the eye-mountable device 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("poly-HEMA"), silicone hydrogels, combinations of these, etc. The polymeric material 220 can be formed with one side having a concave surface 226 suitable to fit over a corneal surface of an eye. The opposite side of the disk can have a convex surface 224 that does not interfere with eyelid motion while the eye-mountable device 210 is mounted to the eye. A circular outer side edge 228 connects the concave surface 224 and convex surface 226.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some examples, the dimensions of the eye-mountable device 210 can be selected according to the size and/or shape of the corneal surface of the wearer's eye.

The polymeric material 220 can be formed with a curved shape in a variety of ways. For example, techniques similar to those employed to form vision-correction contact lenses, such as heat molding, injection molding, spin casting, etc. can be employed to form the polymeric material 220. While the eye-mountable device 210 is mounted in an eye, the convex surface 224 faces outward to the ambient environment while the concave surface 226 faces inward, toward the corneal surface. The convex surface 224 can therefore be considered an outer, top surface of the eye-mountable device 210 whereas the concave surface 226 can be considered an inner, bottom surface. The "bottom" view shown in FIG. 2A is facing the concave surface 226. From the bottom view shown in FIG. 2A, an outer periphery 222, near the outer circumference of the curved disk is curved to extend out of the page, whereas the central region 221, near the center of the disk is curved to extend into the page.

A substrate 230 is embedded in the polymeric material 220. The substrate 230 can be embedded to be situated along the outer periphery 222 of the polymeric material 220, away from the central region 221. The substrate 230 does not interfere with vision because it is too close to the eye to be in focus and is positioned away from the central region 221 where incident light is transmitted to the eye-sensing portions of the eye. Moreover, the substrate 230 can be formed of a transparent material to further mitigate effects on visual perception.

The substrate 230 can be shaped as a circular ring (e.g., a disk with a centered hole). The surface of the substrate 230 (e.g., along the radial width) is a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections. The substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented in a variety of different form factors, similar to the discussion of the substrate 130 in connection with FIG. 1 above.

A loop antenna 270, controller 250, and bio-interactive electronics 260 are disposed on the embedded substrate 230. The controller 250 can be a chip including logic elements configured to operate the bio-interactive electronics 260 and the loop antenna 270. The controller 250 is electrically connected to the loop antenna 270 by interconnects 257 also situated on the substrate 230. Similarly, the controller 250 is electrically connected to the bio-interactive electronics 260 by an interconnect 251. The interconnects 251, 257, the loop antenna 270, and any conductive electrodes (e.g., for an electrochemical analyte bio-sensor, etc.) can be formed from conductive materials patterned on the substrate 230 by a process for precisely patterning such materials, such as deposition, photolithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

As shown in FIG. 2A, bio-interactive electronics 260 is mounted to a side of the substrate 230 facing the convex surface 224. Where the bio-interactive electronics 260 includes an analyte bio-sensor, for example, mounting such a bio-sensor on the substrate 230 facing the convex surface 224 allows the bio-sensor to sense analyte concentrations in tear-film through a channel 272 (shown in FIGS. 2C and 2D) in the polymeric material 220 to the convex surface 224. In some examples, some electronic components can be mounted on one side of the substrate 230, while other electronic components are mounted to the opposing side, and connections between the two can be made through conductive materials passing through the substrate 230.

In an example, the loop antenna 270 is a layer of conductive material patterned along the flat surface of the substrate 230 to form a flat conductive ring. In some instances, the loop antenna 270 can be formed without making a complete loop. For instances, the loop antenna 270 can have a cutout to allow room for the controller 250 and bio-interactive electronics 260, as illustrated in FIG. 2A. However, the loop antenna 270 can also be arranged as a continuous strip of conductive material that wraps entirely around the flat surface of the substrate 230 one or more times. For example, a strip of conductive material with multiple windings can be patterned on the side of the substrate 230 opposite the controller 250 and bio-interactive electronics 260. Interconnects between the ends of such a wound antenna (e.g., the antenna leads) can then be passed through the substrate 230 to the controller 250.

Figure 2D:
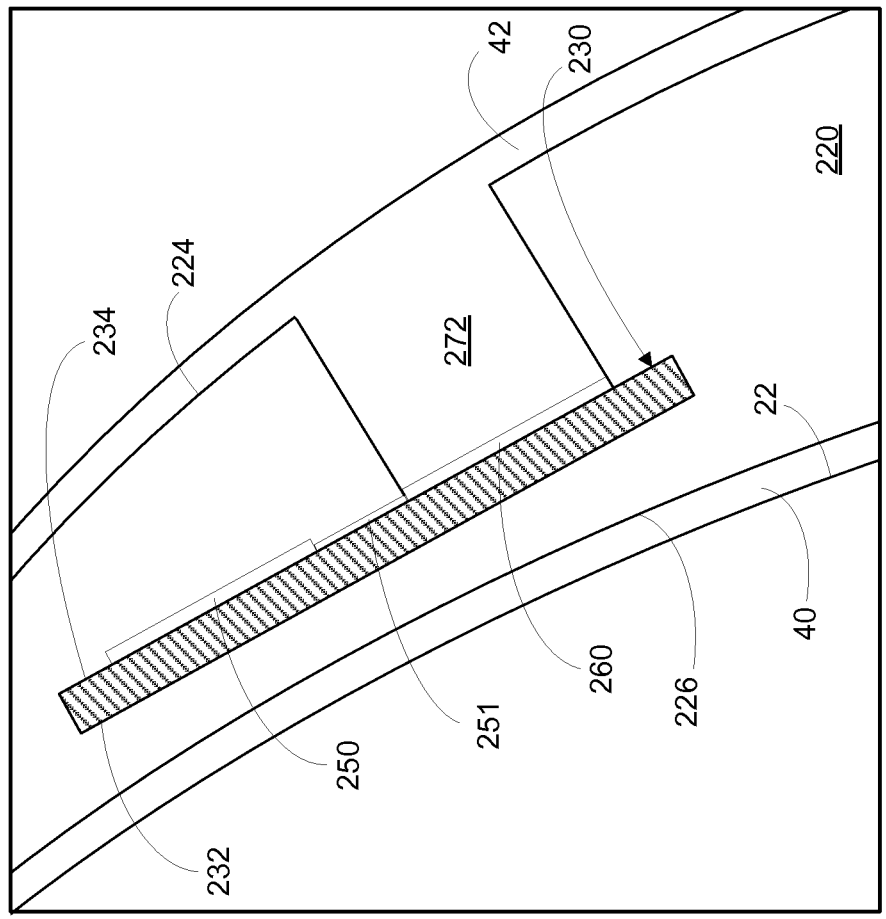
FIG. 2D is a side cross-section view enhanced to show the tear-film layers surrounding the surfaces of the example eye-mountable device when mounted as shown in FIG. 2C, in accordance with an example embodiment.
Figure 2C:
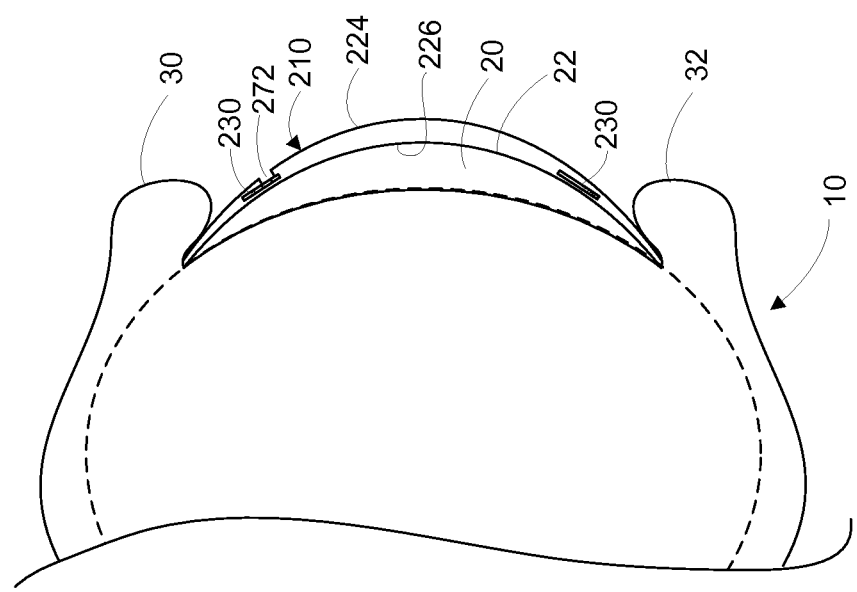
FIG. 2C is a side cross-section view of the example eye-mountable device shown in FIGS. 2A and 2B while mounted to a corneal surface of an eye, in accordance with an example embodiment.

FIG. 2C is a side cross-section view of the example eye-mountable electronic device 210 while mounted to a corneal surface 22 of an eye 10, in accordance with an example embodiment. FIG. 2D is a close-in side cross-section view enhanced to show the tear-film layers 40, 42 surrounding the exposed surfaces 224, 226 of the example eye-mountable device 210, in accordance with an example embodiment. It is noted that relative dimensions in FIGS. 2C and 2D are not necessarily to scale, but have been rendered for purposes of explanation only in describing the arrangement of the example eye-mountable electronic device 210. For example, the total thickness of the eye-mountable device can be about 200 micrometers, while the thickness of the tear-film layers 40, 42 can each be about 10 micrometers, although this ratio may not be reflected in the drawings. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 distributes a tear-film across the exposed corneal surface 22 of the eye 10. The tear-film is an aqueous solution secreted by the lacrimal gland to protect and lubricate the eye 10. When the eye-mountable device 210 is mounted in the eye 10, the tear-film may coat both the concave and convex surfaces 224, 226 with an inner layer 40 (along the concave surface 226) and an outer layer 42 (along the convex layer 224). The tear-film layers 40, 42 can be about 10 micrometers in thickness and together account for about 10 microliters.

The tear-film layers 40, 42 are distributed across the corneal surface 22 and/or the convex surface 224 by motion of the eyelids 30, 32. For example, the eyelids 30, 32 raise and lower, respectively, to spread a small volume of tear-film across the corneal surface 22 and/or the convex surface 224 of the eye-mountable device 210. The tear-film layer 40 on the corneal surface 22 also facilitates mounting the eye-mountable device 210 by capillary forces between the concave surface 226 and the corneal surface 22. In some examples, the eye-mountable device 210 can also be held over the eye in part by vacuum forces against corneal surface 22 due to the concave curvature of the eye-facing concave surface 226.

As shown in the cross-sectional views in FIGS. 2C and 2D, the substrate 230 can be inclined such that the flat mounting surfaces of the substrate 230 are approximately parallel to the adjacent portion of the convex surface 224. As described above, the substrate 230 may be a flattened ring with an inward-facing surface 232 (facing concave surface 226 of the polymeric material 220) and an outward-facing surface 234 (facing convex surface 224). The substrate 230 can have electronic components and/or patterned conductive materials mounted to either or both mounting surfaces 232, 234. As shown in FIG. 2D, the bio-interactive electronics 260, controller 250, and conductive interconnect 251 are mounted on the outward-facing surface 234 such that the bio-interactive electronics 260 are facing convex surface 224.

The polymer layer defining the anterior side of the eye-mountable device 210 of the eye-may be greater than 50 micrometers thick, whereas the polymer layer defining the posterior side of the eye-mountable device 210 may be less than 150 micrometers. Thus, bio-interactive electronics 260 may be at least 50 micrometers away from the convex surface 224 and may be a greater distance away from the concave surface 226. However, in other examples, the bio-interactive electronics 260 may be mounted on the inward-facing surface 232 of the substrate 230 such that the bio-interactive electronics 260 are facing concave surface 226. The bio-interactive electronics 260 could also be positioned closer to the concave surface 226 than the convex surface 224. With this arrangement shown in FIGS. 2C and 2D, the bio-interactive electronics 260 can receive analyte concentrations in the tear-film layer 42 through the channel 272.

III. An Ophthalmic Electrochemical Analyte Sensor

FIG. 3 is a functional block diagram of a system 300 for electrochemically measuring and displaying a tear-film analyte concentration, in accordance with an example embodiment. The system 300 includes an eye-mountable device 210 with embedded electronic components in communication with and powered by reader 180. Reader 180 can also be configured to communicate with display device 350. Reader 180 and eye-mountable device 210 can communicate according to one communication protocol or standard, shown in FIG. 3 as Protocol 1, and reader 180 and display device 350 can communicate according to one communication protocol or standard, shown in FIG. 3 as Protocol 2. In some examples, Protocol 1 and Protocol 2 are the same; while in other examples, Protocol 1 differs from Protocol 2. In particular examples, Protocol 1 is an RFID protocol and Protocol 2 is either a Bluetooth protocol, Wi-Fi protocol, or ZigBee protocol. In other particular examples, Protocol 1 is either a Bluetooth protocol, a Wi-Fi protocol, or a ZigBee protocol. In still other particular examples, Protocol 2 is a wired protocol; such as, but not limited to, a Universal Serial Bus protocol, a Registered Jack protocol (e.g., RJ-25), or a wired Local Area Network protocol (e.g., Ethernet).

The eye-mountable device 210 includes an antenna 312 for capturing radio frequency (RF) power 341 from the reader 180. In some examples, RF power 341 and/or backscatter communication 343 can be provided in accordance with a communications standard or protocol, such as Protocol 1 shown in FIG. 3.

The eye-mountable device 210 includes rectifier 314, energy storage 316, and regulator 318 for generating power supply voltages 330, 332 to operate the embedded electronics. The eye-mountable device 210 includes an electrochemical sensor 320 with a working electrode 322 and a reference electrode 323 driven by a sensor interface 321. The eye-mountable device 210 includes logic 324 (e.g., software or hardware logic) for communicating results from the sensor 320 to the reader 180 by modulating the impedance of the antenna 312. An impedance modulator 325 (shown symbolically as a switch in FIG. 3) can be used to modulate the antenna impedance according to instructions from the logic 324. Similar to the eye-mountable device 110 discussed above in connection with FIG. 1, the eye-mountable device 210 can include a mounting substrate embedded within a polymeric material configured to be mounted to an eye.

The electrochemical sensor 320 can be situated on a mounting surface of such a substrate proximate to the surface of the eye (e.g., corresponding to the bio-interactive electronics 260 on the inward-facing side 232 of the substrate 230) to measure analyte concentration in a tear-film layer interposed between the eye-mountable device 210 and the eye (e.g., the inner tear-film layer 40 between the eye-mountable device 210 and the corneal surface 22). In some examples, however, an electrochemical sensor can be situated on a mounting surface of such a substrate distal from the surface of the eye (e.g., corresponding to the outward-facing side 234 of the substrate 230) to measure analyte concentration in a tear-film layer coating the exposed surface of the eye-mountable device 210 (e.g., the outer tear-film layer 42 interposed between the convex surface 224 of the polymeric material 210 and the atmosphere and/or closed eyelids).

With reference to FIG. 3, a reagent may be localized proximate the electrochemical sensor 320 so as to selectively react with an analyte in the tear-film. The electrochemical sensor 320 measures analyte concentration by applying a voltage between the electrodes 322, 323 that is sufficient to cause products of the analyte catalyzed by the reagent to electrochemically react (e.g., a reduction and/or oxidization reaction) at the working electrode 322. The electrochemical reactions at the working electrode 322 generate an amperometric current that can be measured at the working electrode 322. The sensor interface 321 can, for example, apply a reduction voltage between the working electrode 322 and the reference electrode 323 to reduce products from the reagent-catalyzed analyte at the working electrode 322. Additionally or alternatively, the sensor interface 321 can apply an oxidization voltage between the working electrode 322 and the reference electrode 323 to oxidize the products from the reagent-catalyzed analyte at the working electrode 322. The sensor interface 321 measures the amperometric current and provides an output to the logic 324. The sensor interface 321 can include, for example, a potentiostat connected to both electrodes 322, 323 to simultaneously apply a voltage between the working electrode 322 and the reference electrode 323 and measure the resulting amperometric current through the working electrode 322.

In other embodiments, sensor 320 can further include and/or be replaced by sensor(s) that measure light, heat/temperature, blood pressure, air flow, and/or other characteristics than analyte concentration(s). In these other embodiments, sensor 320 can communicate data about the measured characteristics to reader 180 using backscatter communication 343 as discussed below.

The rectifier 314, energy storage 316, and voltage regulator 318 operate to harvest energy from received RF power 341. RF power 341 causes radio frequency electrical signals on leads of the antenna 312. The rectifier 314 is connected to the antenna leads and converts the radio frequency electrical signals to a DC voltage. The energy storage 316 (e.g., capacitor) is connected across the output of the rectifier 314 to filter out high frequency components of the DC voltage. For instance, the regulator 318 may receive the filtered DC voltage and output both a digital supply voltage 330 to operate the logic 324 and an analog supply voltage 332 to operate the electrochemical sensor 320. For example, the analog supply voltage 332 can be a voltage used by the sensor interface 321 to apply a voltage between the sensor electrodes 322, 323 to generate an amperometric current. The digital supply voltage 330 can be a voltage suitable for driving digital logic circuitry, such as approximately 1.2 volts, approximately 3 volts, etc. Reception of the RF power 341 from the reader 180 (or another source, such as ambient radiation, etc.) causes the supply voltages 330, 332 to be supplied to the sensor 320 and logic 324. While powered, the sensor 320 and logic 324 are configured to generate and measure an amperometric current and communicate the results.

The sensor results can be communicated back to the reader 180 via backscatter radiation 343 from the antenna 312. The logic 324 receives the output current from the electrochemical sensor 320 and modulates (325) the impedance of the antenna 312 in accordance with the amperometric current measured by the sensor 320. The antenna impedance and/or change in antenna impedance are detected by the reader 180 via the backscatter signal 343.

Reader 180 can include Protocol 1 front end 342a and logic components 344 to communicate using Protocol 1, decode the information indicated by the backscatter signal 343, provide digital inputs to a processing system 346 and receive inputs and/or provide outputs via user interface 348. Protocol 1 can be, for example, an RFID protocol. In some examples, part or all of eye-mountable device 210 can be configured to perform some or all features of an RFID tag. For example, as shown in FIG. 3, some or all of the components shown as tag 370 of eye-mountable device 210 can perform some or all features of an RFID tag; e.g., antenna 312, rectifier 314, energy storage 316, voltage regulator 318, logic 324, etc.

In some examples, one or more of the features shown as separate functional blocks can be implemented ("packaged") on a single chip. For example, the eye-mountable device 210 can be implemented with the rectifier 314, energy storage 316, voltage regulator 318, sensor interface 321, and the logic 324 packaged together in a single chip or controller module. Such a controller can have interconnects ("leads") connected to the loop antenna 312 and the sensor electrodes 322, 323. Such a controller operates to harvest energy received at the loop antenna 312, apply a voltage between the electrodes 322, 323 sufficient to develop an amperometric current, measure the amperometric current, and indicate the measured current via the antenna 312 (e.g., through the backscatter radiation 343).

A processing system, such as, but not limited to, processing system 346 or processing system 356, can include one or more processors and one or more storage components. Example processor(s) include, but are not limited to, CPUs, Graphics Processing Units (GPUs), digital signal processors (DSPs), application specific integrated circuits (ASICs). Example storage component(s) include, but are not limited to volatile and/or non-volatile storage components, e.g., optical, magnetic, organic or other memory, disc storage; Random Access Memory (RAM), Read-Only Memory (ROM), flash memory, optical memory unit, and disc memory. The storage component(s) can be configured to store software and data; e.g., computer-readable instructions configured, when executed by a processor of the processing system 346 or 356, to cause the processing system 346 or 356 to carry out functions such as but not limited to the herein-described functions of reader 180, eye-mountable device 210, and/or display device 350.

The reader 180 can associate the backscatter signal 343 with the sensor result (e.g., via the processing system 346 according to a pre-programmed relationship associating impedance of the antenna 312 with output from the sensor 320). The processing system 346 can then store the indicated sensor results (e.g., tear-film analyte concentration values) in a local memory and/or an external memory (e.g., by communicating with the external memory either on display device 350 or through a network).

User interface 348 of reader 180 can include an indicator, such as but not limited to one or more light-emitting diodes (LEDs), that can indicate that reader 180 is operating and provide some information about its status. For example, reader 180 can be configured with an LED that displays one color (e.g., green) when operating normally and another color (e.g., red) when operating abnormally. In other embodiments, the LED(s) can change display when processing and/or communicating data in comparison to when idle (e.g., periodically turn on and off while processing data, constantly stay on or constantly stay off while idle).

In some examples, one or more of the LED(s) of user interface 348 can indicate a status of sensor data; e.g., not display when sensor data are either within normal range(s) or unavailable, display in a first color when sensor data are either outside normal range(s) but not extremely high or low, and display a second color when the sensor data are extremely high and/or low. For example, if sensor data indicate that blood-glucose levels are extremely high or low, user interface 348 can be instructed by processing system 346 to display using the second color. In particular examples, user interface 348 can include a speaker or other sound-emitting device to permit reader 180 to generate sounds; e.g., warning sound(s) and/or tone(s) if sensor data are extremely high and/or low.

In still other examples, reader 180 can have one or more buttons and/or other devices to receive inputs. For example, reader 180 can have a calibration button to indicate when calibration data is to be generated.

In some examples, reader 180 can communicate with devices in addition to eye-mountable device 210/tag 370. For example, FIG. 3 shows communication 360 between reader 180 and display device 350 using Protocol 2.

To communicate with display device 350, reader 180 can include Protocol 2 front end 342*b* and logic 344 can be configured to use Protocol 2 front end 342*b* to communicate using Protocol 2. In some examples, processing system 346 can be configured to include and/or perform the herein-described functionality of logic 344.

FIG. 3 shows that display device 350 can include Protocol 2 front end 352, logic 354, processing system 356, and user interface (UI) 358. Logic 354 can be configured to use Protocol 2 front end 352 to communicate using Protocol 2 with at least reader 180. Processing system 356 can include computer-readable instructions that, when executed, are configured to perform some or all the herein-described functions of display system 350. In some examples, processing system 356 can be configured to include and/or perform the herein-described functionality of logic 354. UI 358 can be configured with hardware and/or software configured to present images, text, sound, haptic feedback, etc., such as, but not including, presenting images, graphs, text, audio, and/or video information related to data received from reader 180 as part of communication 360. See FIG. 8 for an example view that can be provided by display device 350.

In some examples, display device 350 can include Protocol 3 front end 362. In these embodiments, logic 354 can be configured to use Protocol 3 front end 362 to for sending and receiving communications 364 using Protocol 3 with one or more other devices (such as an insulin delivery pump not shown in FIG. 3). Protocol 3 can include one or more wireless protocols, such as, but not limited to, a RFID protocol, a Bluetooth protocol, a Wi-Fi protocol, a ZigBee protocol, a WiMax protocol, or a Wireless Wide Area Network protocol (e.g., TDMA, CDMA, GSM, UMTS, EV-DO, LTE) and/or one or more wired protocols; such as, but not limited to, a Universal Serial Bus protocol, a Registered Jack protocol (e.g., RJ-25), or a wired Local Area Network protocol (e.g., Ethernet). In an example, Protocol 2 front end 352 and Protocol 3 front end 362 can be combined.

In examples utilizing Protocol 3, display device 350 can be used to forward and/or bridge data with the one or more other devices. In one example, a device of the one or more other devices can be a server configured to run one or more applications for collecting data from display device 350; e.g., a cloud data collection application. In another example, the other device can be an insulin delivery device or pump configured to inject insulin at a given delivery rate into a blood stream of a patient based on communication with the reader 180.

IV. Example Electrochemical Sensor

Figure 4A:
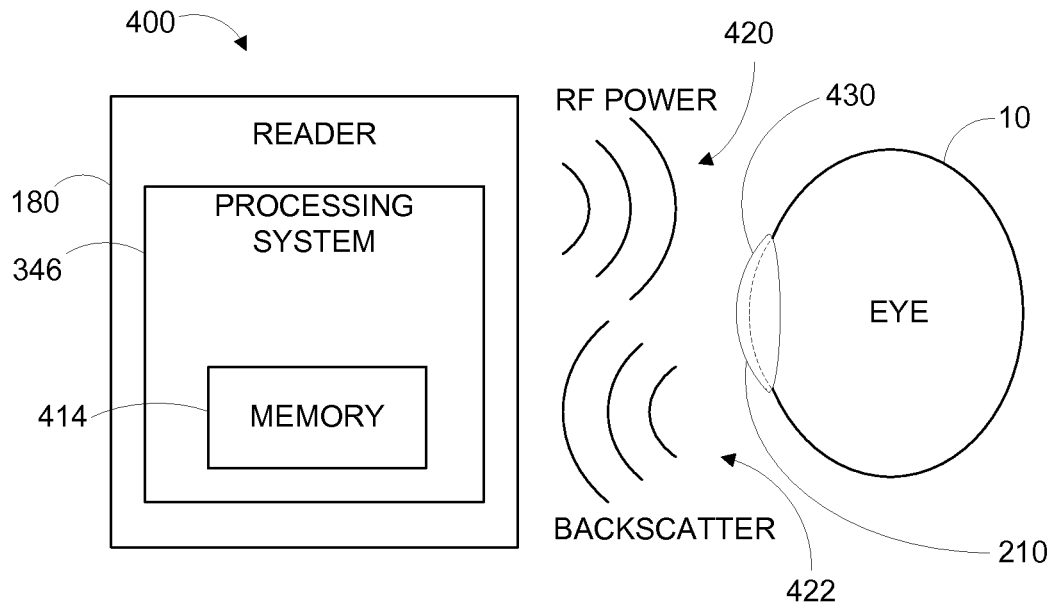
FIG. 4A is a block diagram of an ophthalmic electrochemical sensor system operated by a reader to obtain a series of amperometric current measurements over time, in accordance with an example embodiment.

FIG. 4A is a block diagram of a system 400 with eye-mountable device 210 operated by a reader 180 to obtain a series of amperometric current measurements over time, in accordance with an example embodiment. An ophthalmic electrochemical sensor; e.g., an embodiment of sensor 320, can be included with eye-mountable device 210. As shown in FIG. 4A, eye-mountable device 210 is configured to be contact-mounted over a corneal surface of an eye 10. The ophthalmic electrochemical sensor can be operated to be transitioned into an active measurement mode in response to receiving a measurement signal from the reader 180.

The reader 180 includes a processing system 346, configured with memory 414. The processing system 346 can be a computing system that executes computer-readable instruction stored in the memory 414 to cause the reader 180/system 400 to obtain a time series of measurements by intermittently transmitting a measurement signal to eye-mountable device 210. In response to the measurement signal, one or more sensors of eye-mountable device 210; e.g., ophthalmic electrochemical sensor 430, can take measurement(s), obtain results of the measurement(s), and communicate the results as shown in connection to reader 180 via backscatter 422. As discussed above regarding FIG. 3, reader 180 can provide RF power, such as RF power 420, to be harvested by the eye-mountable device 210. For example, impedance of an antenna of eye-mountable device 210 can be modulated in accordance with the sensor result such that the backscatter radiation 422 indicates the sensor results. Reader 180 can also use memory 414 to store indications of amperometric current measurements communicated by the ophthalmic electrochemical sensor 430. The reader 180 can thus be operated to intermittently power the ophthalmic electrochemical sensor 430 so as to obtain a time series of amperometric current measurements.

Figure 4B:
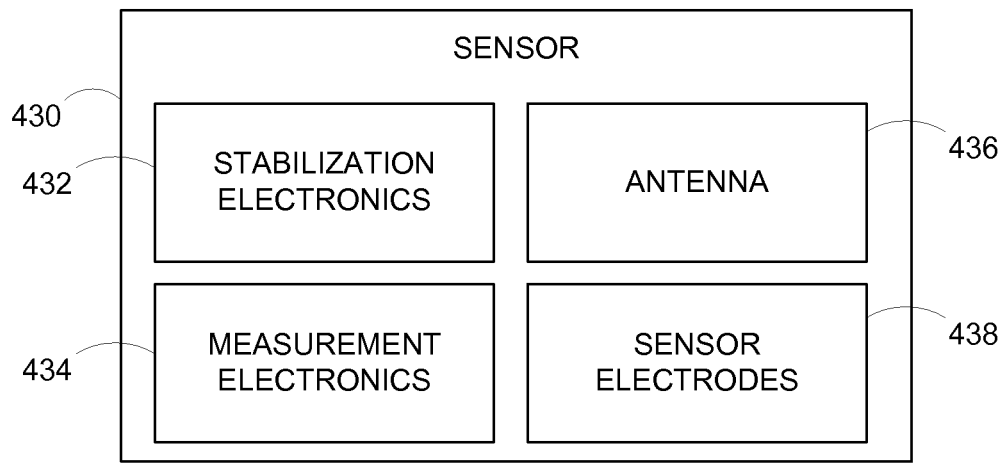
FIG. 4B is a block diagram of the ophthalmic electrochemical sensor system described in connection with FIG. 4A, in accordance with an example embodiment.

FIG. 4B is a block diagram of the ophthalmic electrochemical sensor 430 described in connection with FIG. 4A, in accordance with an example embodiment. The ophthalmic electrochemical sensor 430 can include stabilization electronics 432, measurement electronics 434, an antenna 436, and sensor electrodes 438. The stabilization electronics 432 can be configured to apply a stabilization voltage between the sensor electrodes 438 while the ophthalmic electrochemical sensor 430 is operating in a standby (or stabilization) mode. The measurement electronics 434 are configured to measure the amperometric current through the working electrode of the sensor electrodes 438 and communicate the measured amperometric current through the antenna 436.

Ophthalmic electrochemical sensor 430 can include energy harvesting systems for harvesting energy from incident radiation (and/or other sources) to generate bias voltage to apply across sensor electrodes during the standby mode. Ophthalmic electrochemical sensor 430 can also be configured to generate power from incident radiation to power measurement and communication electronics in response to receiving a measurement signal indicating initiation of an active measurement mode. For example, measurement electronics 434 can be configured to harvest energy from incident radio frequency radiation via the antenna 436 and use the harvested energy to power the measurement and communication of the amperometric current.

V. Example Eye-Proximate Readers

Figure 5:
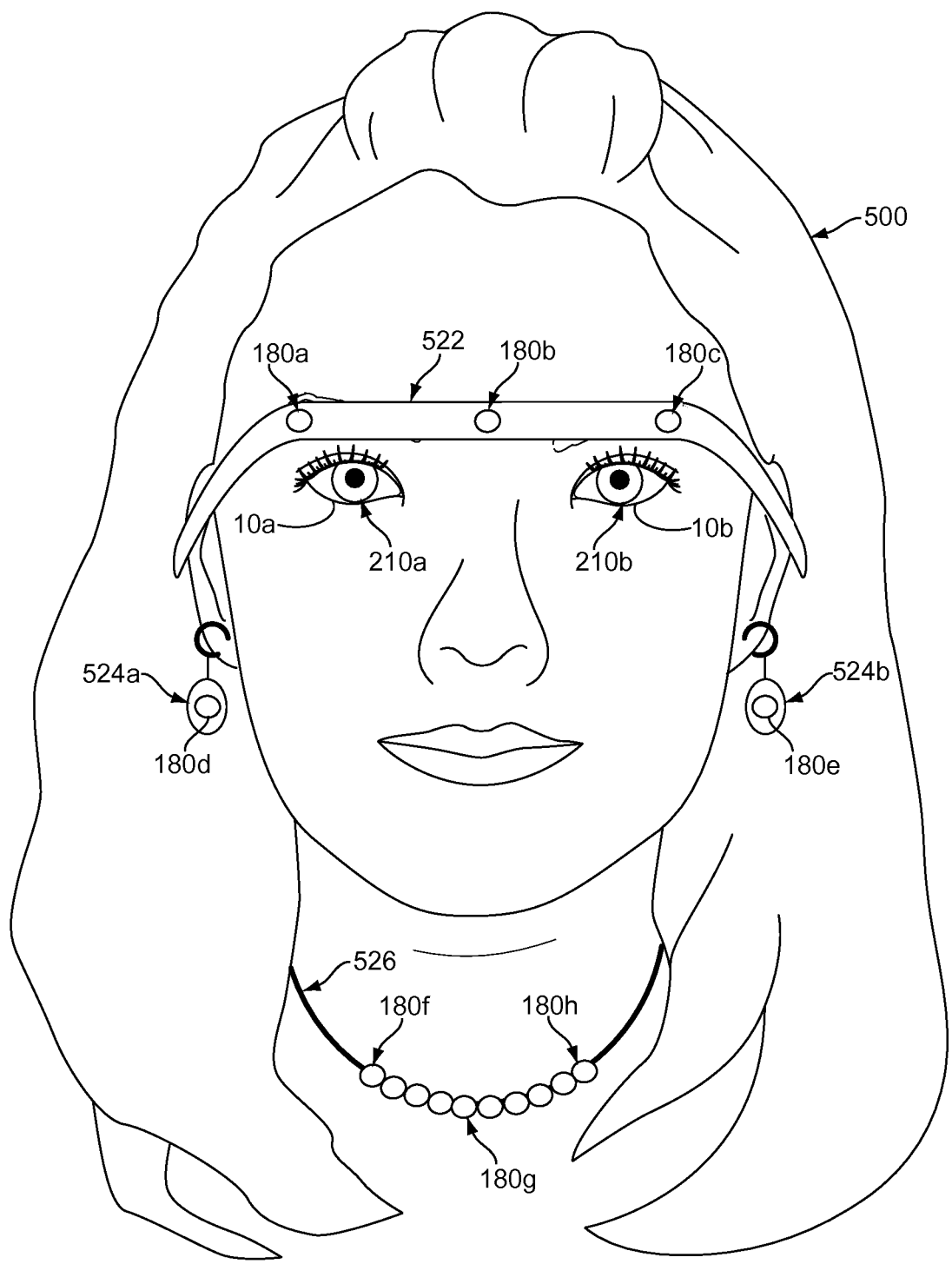
FIG. 5 shows an example wearer wearing two eye-mountable devices and one or more readers, in accordance with an example embodiment.

FIG. 5 shows an example wearer 500 wearing two eye-mountable devices 210a, 210b, a band 522, earrings 524a, 524b, and a necklace 526, in accordance with an example embodiment. As discussed above at least in the context of FIGS. 3, 4A, and 4B, each eye-mountable device 210a, 210b can be configured with sensor(s) to take measurements relating to analytes in the tear-film of an eye that the respective lens is worn in.

The functionality of band 522 can be performed by a structure of another device, e.g., an eye-glass frame, a head-mountable computer frame, a head-mounted display (HMD), a cap, a hat, part of a hat or cap (e.g., a hat band or bill of a baseball cap), a headphone headband, etc., or by a separate band; e.g., a head band, a scarf or bandanna worn as a head band. For examples, band 522 can be supported by ear(s), nose, hair, skin, and/or a head of wearer 500, and perhaps by external devices e.g., stick pins, bobby pins, headband elastics, snaps. Other and different support(s) for band 522 are possible as well.

One or more of band 522, earrings 524a, 524b, and necklace 526 can be configured to include one or more readers; e.g., the above-mentioned reader 180. FIG. 5 shows three example positions 180a, 180b, and 180c for readers in band 522. For example, if eye-mountable device 210a has a sensor, then a reader, such as reader 180, can be mounted in example positions 180a and/or 180b to send commands and power to eye-mountable device 210a. Similarly, to power and communicate with a sensor in eye-mountable device 210b, a reader mounted in band 522, such as reader 180, can be mounted in example positions 180b and/or 180c.

Each of or both earrings 524a, 524b can be configured with respective readers 180d, 180e for communicating with and power sensors in respective eye-mountable devices 210a, 210b. Necklace 526 can be configured with one or more readers 180f, 180g, 180h for communicating with and power sensors in respective eye-mountable device 210a, 210b. Other embodiments are possible as well; e.g., readers in positions 180a-180c or near those positions can be configured as part of a hat, headband, scarf, jewelry (e.g., a brooch), glasses, HMD, and/or other apparatus.

In some examples, a reader can power a sensor in eye-mountable device 210 using a low-power transmission; e.g., a transmission of 1 watt or less of power. In these examples, the reader 180 can be within a predetermined distance; e.g., 1 foot, 40 cm, of eye-mountable device 210a, 210b to power the sensor.

VI. Example Glucose Level Control System

Diabetes patients may take insulin medications to control high glucose levels to prevent hyperglycemia, which is a condition that occurs when an excessive amount of blood sugar (glucose) circulates in the blood plasma (e.g., glucose level above 200 milligram/deciliter). However, inaccurate control of insulin medication amounts taken by a patient may cause hypoglycemia, which is a condition that occurs when glucose is below a certain level (e.g., 70 milligram/deciliter). Hyperglycemia and hypoglycemia are both harmful to the patient. A closed loop feedback control of patient glucose levels that is configured to control an insulin delivery device based on continuous monitoring of glucose levels may facilitate maintaining the glucose level between target values to prevent both hyperglycemia and hypoglycemia.

Figure 6:
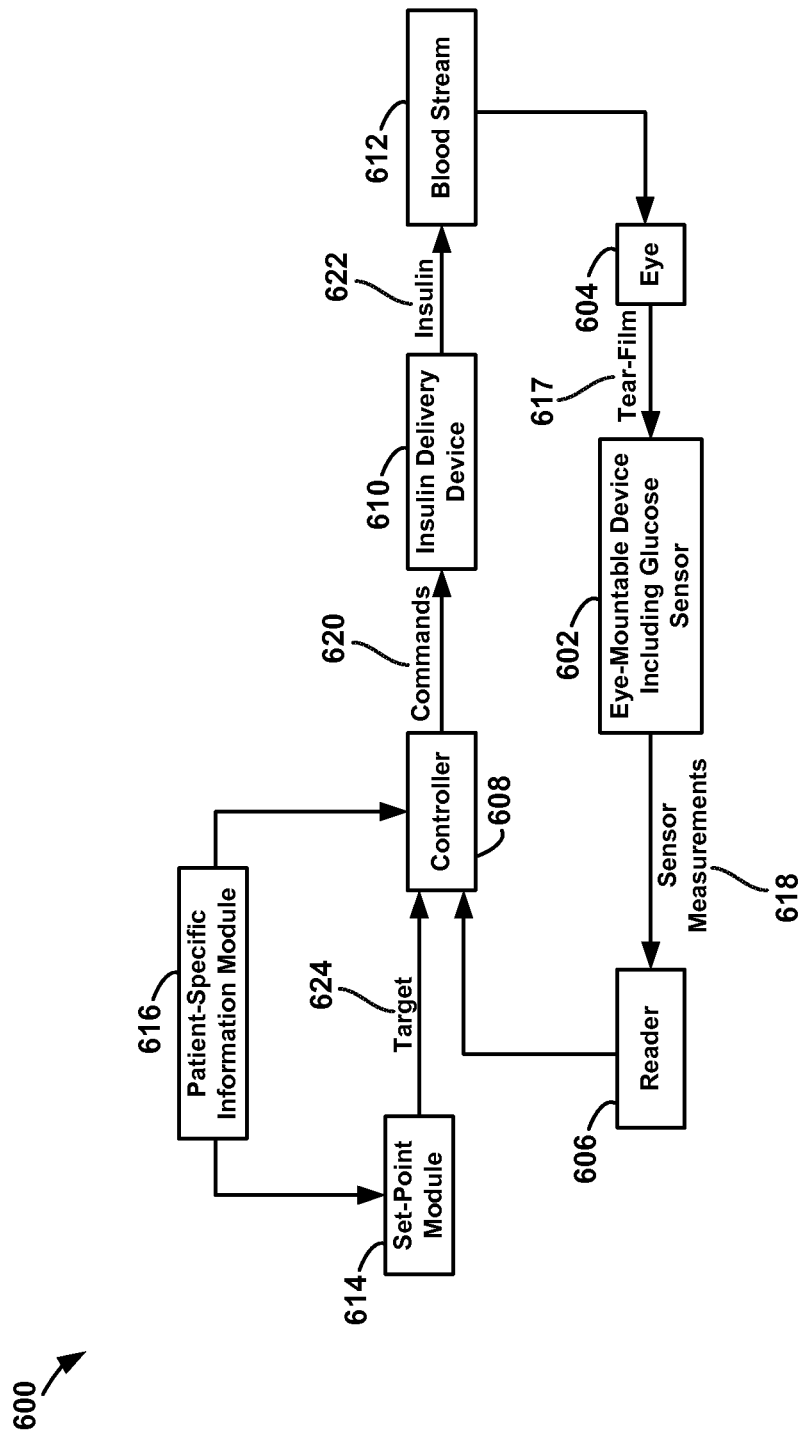
FIG. 6 is a block diagram of a glucose control system, in accordance with an example embodiment.

FIG. 6 is a block diagram of a glucose control system 600, in accordance with an example embodiment. FIG. 6 depicts an eye-mountable device 602 (e.g., the eye-mountable device 110 or 210) mounted to an eye 604 and in communication with a reader 606 (e.g., the reader 180 described above). The reader 606 is in communication with a controller 608 configured to control an insulin delivery device 610, which is configured to inject insulin into a blood stream 612. The controller 608 may have access to a set-point module 614 and a patient-specific information module 616. The set-point module 614 may also be in communication with the patient-specific information module 616.

In examples, a tear-film 617 secreted from the lacrimal gland to coat the eye 604 is in contact with the blood stream 612 through capillaries in the structure of the eye 604. The tear film 617 may thus include biomarkers found in the blood stream 612, such as glucose, that can be analyzed to characterize a person's health condition(s). The glucose concentration in the tear-film 617 can be different from the corresponding concentration of the glucose in the blood stream 612, but a relationship between the two concentration levels can be established to map tear-film glucose concentration values to blood concentration levels. The eye-mountable device 602 includes an electrochemical glucose sensor (e.g., the sensor 162, 320, or 430) configured to measure glucose concentration in the tear-film 617. As described above with respect to the sensors 162, 320, and 430, the glucose sensor may include, or interface with, sensor electrical components to provide power to the sensor and to generate sensor signals, a sensor communication system to interface with the reader 606, etc.

The system 600 includes the reader 606 configured to be in communication with the eye-mountable device 602 and the glucose sensor coupled thereto. The reader 606 may receive (e.g., via a wireless interface) indications of one or more sensor measurements 618 taken by the glucose sensor. The reader 606 may be configured to provide information related to the sensor measurements 618 to the controller 608. In examples, the reader 606 may be configured to determine the blood glucose level based on the sensor measurements 618 and provide the determined glucose level to the controller 608. In another example, the reader 606 may provide the indications of the sensor measurements 618 to the controller and the controller may be configured to determine the glucose level. In still another example, the glucose level may be established by both the reader 606 and the controller 608 for comparison and calibration purposes.

The controller 608 may be configured to generate instructions or commands 620 that are communicated to the insulin delivery device 610 (e.g., any type of insulin pump). The controller 608 may be configured to communicate the commands 620 to the insulin delivery device 610 wirelessly using any available wireless protocol or via a wired connection. The insulin delivery device 610 may receive the commands 620 and infuse insulin 622 into the blood stream 612 in response to the commands 620.

In examples, the controller 608 may include electrical components and software to generate the commands 620 for the insulin delivery device 610. The controller 608 may also include a controller communication system to receive information from the reader 606 and provide the commands 620 to the insulin delivery device 610. In an example, the controller 608 may include a user interface and/or operator interface (not shown) comprising a data input device and/or a data output device. The data output device may, for example, generate signals to initiate an alarm and/or include a display or printer for showing status of the controller 608 and/or a patient's vital indicators. The data input device may comprise dials, buttons, pointing devices, manual switches, alphanumeric keys, a touch-sensitive display, combinations thereof, and/or the like for receiving user and/or operator inputs. Other input and output device are possible as well.

The controller 608 may also obtain a target glucose level 624 from the set-point module 614 and/or the patient specific information module 616. The set-point module 614 may be configured to provide the target glucose level 624 to the controller 608 based on stored information. In an example, the set-point module 614 may be configured to continuously adjust the target level 624 based on information received from the patient-specific information 616. For example, every patient may be different and may have a different target level appropriate for the patient's condition. The patient-specific information module 616 may be configured to store patient's information (e.g., based on inputs by patient or physician treating patient with permission from the patient) such as age, previous history of treatment, information related to history of response of patients to dosages of insulin, and any other information that can be utilized by the controller 608 to provide proper commands 620 to the insulin delivery device 610. The patient-specific information module 616 may continuously be updated with new information over time. The set-point module 614 in communication with the patient-specific information module 616 may thus adjust the target glucose level 624 based on any patient-specific information or updates thereof.

The controller 608 may be configured to compare the target glucose level 624 to a current blood glucose level received or fed back from the reader 606 or determined by the controller 608 based on information received from the reader 606 (information indicative of the sensor measurements 618). Based on the comparison, the controller 608 may be configured to provide the commands 620 to the insulin delivery device 610. For example, the controller 608 may be configured to implement any form of close loop control techniques such as proportional, integral, derivative (PID) control, robust control, model-predictive control, adaptive control, etc. that provide the commands 620 based on a discrepancy between the current blood glucose level and the target glucose level 624. An example adaptive controller 608 may be configured to include a learning algorithm that monitors patient response to doses of insulin over time and takes into consideration information provided by the patient-specific information module 616 and any other changes to adapt or tailor the commands 620 for enhanced control of glucose level in the blood stream 612 of a specific patient.

In one example, the controller 608 may be configured to receive information related to the sensor measurements 618 over time and establish a pattern of change or a rate of change of glucose concentration in the blood stream 612. The rate of change of glucose concentration may be indicative of a patient's response to insulin injections over time, for example. The rate of change may also be indicative of other health conditions of the patient. In this example, the controller 608 may be configured to take the rate of change of glucose concentration into consideration when providing the commands 620 to the insulin delivery device.

In another example, instead of or in addition to establishing the target glucose concentration 624, the set-point module 614 may be configured to establish a range of glucose concentration about the target glucose concentration 624 that may be considered healthy for a given patient. For instance, the range may be fixed or may be based on patient-specific information received from the patient-specific information module 616. In this example, the controller 608 may be configured to provide the commands 620 such that the insulin delivery device 610 maintains a predetermined insulin delivery rate when the glucose concentration is within the range. If the glucose concentration deviates from the range, the controller 608 may be configured to provide the commands 620 such that the insulin delivery device 610 changes the insulin delivery rate to the blood stream 612 so as to bring the glucose concentration in the blood stream 612 within the range.

The insulin delivery device 610 may include an infusion device and/or an infusion tube to infuse insulin 622 into the blood stream 612 at a given rate. For example, the commands 620 may be provided to the insulin delivery device 610 by the controller 608 so as to control the insulin delivery rate/dosages over time. In examples, the insulin 622 may be infused using an intravenous system for providing fluids to a patient (e.g., in a hospital or other medical environment).

In examples, an infusion device (not explicitly identified in FIG. 6) may include infusion electrical components to activate an infusion motor according to the commands 620, an infusion communication system to receive the commands 620 from the controller 608, and an infusion device housing (not shown) to hold the infusion device.

In some examples, the controller 608 may be housed in the infusion device housing, and an infusion communication system may comprise an electrical trace or a wire that carries the commands 620 from the controller 608 to the infusion device. Thus, the controller 608 and the insulin delivery device 610 may be co-located or integrated together. In other examples, the controller 608 may be integrated into the reader 606. For example, the reader 606 may include a processing system (e.g., the processing system 346 shown in FIG. 3) and the controller 608 may be integrated into such processing system. In still another example, the controller 608 may have its own housing or may be included in a supplemental device. For instance, the controller 608 may be integrated into a mobile phone (e.g., an application installed on the mobile phone), a wearable computing device worn by the patient, a laptop or desktop in wired or wireless communication with the reader 606 and the insulin delivery device 610, etc. In yet still another example, the controller 608 may be located at a remote server in wireless communication (e.g., using WiFi, CDMA, WiMAX, GSM, etc. interfaces) with the reader 606 and the insulin delivery device 610. In further examples, components of the system 600 such as the eye-mountable device 602, the reader 606, the controller 608, and the insulin delivery device 610 may utilize a cable, a wire, a fiber optic line, radio frequency, infrared signals, or ultrasonic transmitters and receivers, or a combination thereof for communication with each other.

The system 600 thus illustrates a closed loop feedback control of patient glucose levels that is configured to control an insulin delivery device based on continuous monitoring of glucose levels. In this manner, the control system 600 may facilitate maintaining the glucose level between target values to prevent both hyperglycemia and hypoglycemia.

Components of the system 600 may be configured to work in an interconnected fashion with each other and/or with other components coupled to respective systems. One or more of the described functions, components, or blocks of the system 600 may be divided up into additional functional or physical components, or combined into fewer functional or physical components. For example, the set-point module 614 may be integrated into the controller 608. The controller 608 may be integrated into the insulin delivery device 610 or the reader 608. In some further examples, additional functional and/or physical components may be added to the examples illustrated by FIG. 6. For example, the system 600 may include a filter (or a pre-filter) configured to filter and process signals from the sensor before the signals are provided to the reader 606 or the controller 608. The system 600 may include a processor (e.g., a microprocessor, a digital signal processor (DSP), etc.) configured to execute program code including one or more instructions for implementing logical functions described with respect to the controller 608. The system 600 may further include any type of computer readable medium (non-transitory medium) or memory, for example, such as a storage device including a disk or hard drive, to store the program code. In other examples, the system 600 may be included within other systems.

VII. Example Method For Controlling Glucose Concentration

Figure 7:
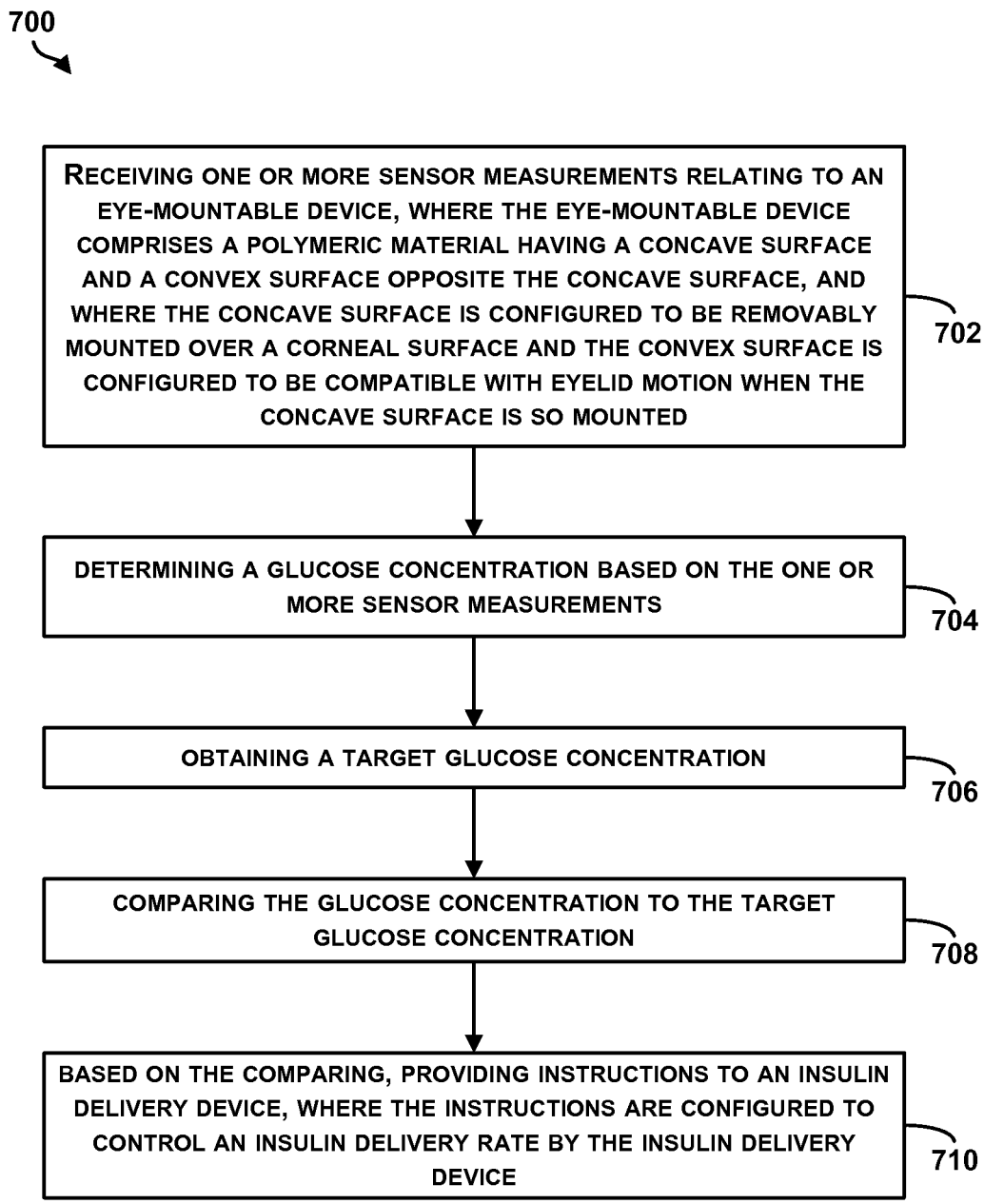
FIG. 7 is a flow chart of a method for controlling glucose levels, in accordance with an example embodiment.

FIG. 7 is a flow chart of a method 700 for controlling glucose levels, in accordance with an example embodiment. The method 700 may include one or more operations, functions, or actions as illustrated by one or more of blocks 702-710. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation In addition, for the method 700 and other processes and methods disclosed herein, the flowchart shows functionality and operation of one possible implementation of present examples. In this regard, each block may represent a module, a segment, or a portion of program code, which includes one or more instructions executable by a processor for implementing specific logical functions or steps in the process. The program code may be stored on any type of computer readable medium or memory, for example, such as a storage device including a disk or hard drive. The computer readable medium may include a non-transitory computer readable medium or memory, for example, such as computer-readable media that stores data for short periods of time like register memory, processor cache and Random Access Memory (RAM). The computer readable medium may also include non-transitory media or memory, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, a tangible storage device, or other article of manufacture, for example. In addition, for the method 700 and other processes and methods disclosed herein, each block in FIG. 7 may represent circuitry that is wired to perform the specific logical functions in the process.

At block 702, the method 700 includes receiving one or more sensor measurements relating to an eye-mountable device. The eye-mountable device comprises a polymeric material having a concave surface and a convex surface opposite the concave surface. The concave surface is configured to be removably mounted over a corneal surface and the convex surface is configured to be compatible with eyelid motion when the concave surface is so mounted.

Figure 8:
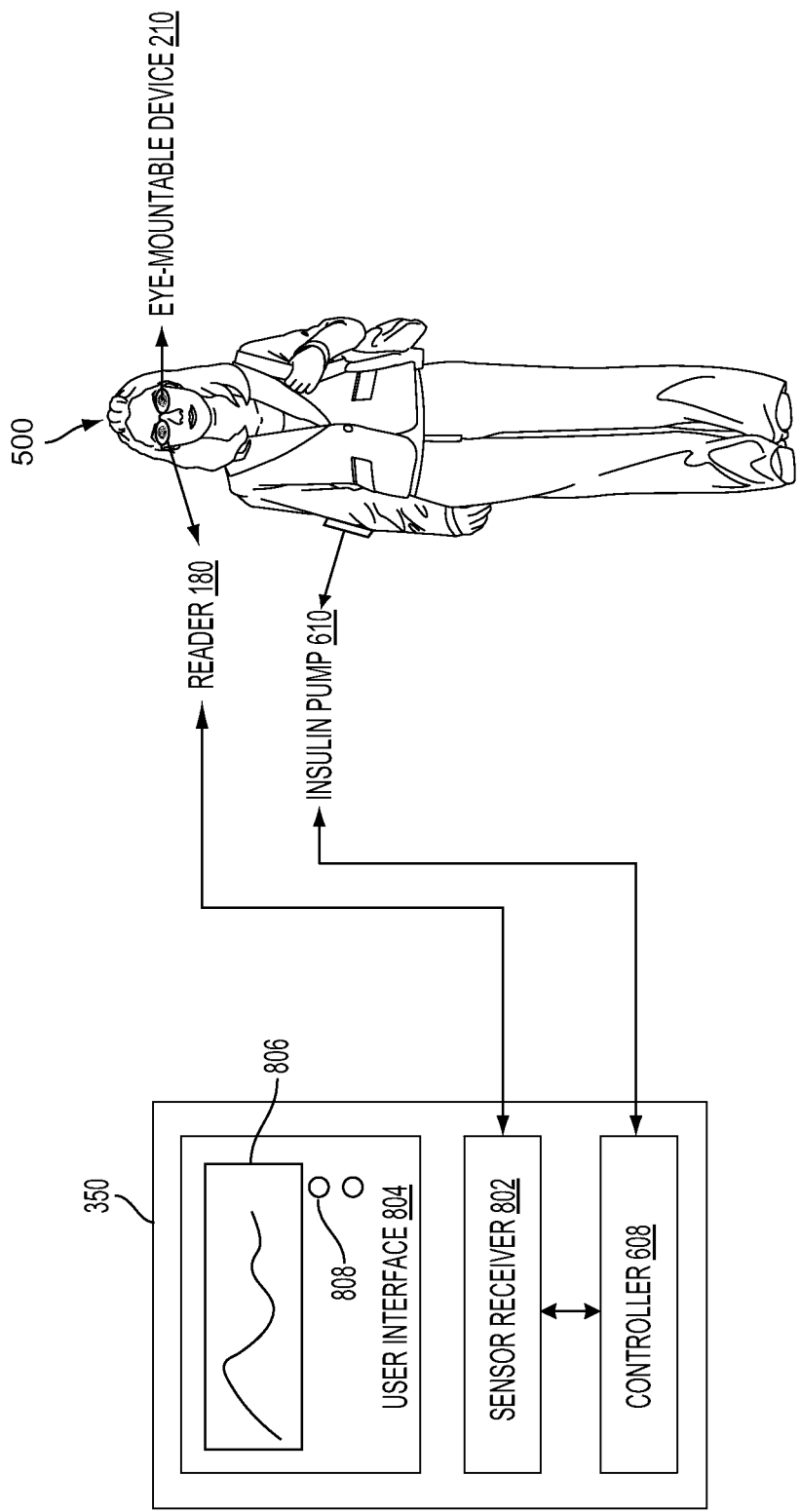
FIG. 8 is an example system for controlling glucose levels, in accordance with an example embodiment.

FIG. 8 is an example system for controlling glucose levels, in accordance with an example embodiment. The patient 500 may be wearing the eye-mountable device 210 (210a and 210b if an eye-mountable device is worn in each eye). The eye-mountable device 210 may be similar in functionality to the eye-mountable devices 110 and 602 described above, for example. As described above with respect to FIGS. 2A-2D, the eye-mountable device 210 includes the polymeric material 220, which can be formed with one side having the concave surface 226 suitable to fit over a corneal surface of an eye. The opposite side of the disk can have the convex surface 224 that does not interfere with eyelid motion while the eye-mountable device 210 is mounted to the eye.

The eye-mountable device 210 may be contacting a tear-film and may also include an electrochemical or glucose sensor (e.g., any of the sensors 162, 320, and 430 described above) configured to provide sensor measurements related to the tear-film to the reader 180 (i.e., any of the readers 180a-g shown in FIG. 5). The reader 180 may have the same functionality described with respect to the reader 606 described above, for example.

Referring back to FIG. 7, at block 704, the method 700 includes determining a glucose concentration based on the one or more sensor measurements. In an example, the reader 180 shown in FIG. 8 may be configured to process the sensor measurements to determine glucose concentration in the tear-film contacting the eye-mountable device 210. Based on the glucose concentration in the tear-film, the reader 180 may be configured to determine a blood glucose concentration for the patient 500 based on a predetermined (e.g., empirical) relationship between the glucose concentration in the tear-film and the corresponding blood glucose concentration. Further, the reader 180 may be configured to provide the blood glucose concentration to the controller 608. The controller 608 may be embedded as a module (software or hardware) in the display device 350 as shown in FIG. 8. In another example, the reader 180 may be configured to provide raw sensor measurements to a sensor receiver 802. The sensor receiver 802 may process (e.g., filter) the sensor measurements and provide information related to the sensor measurements to the controller 608. The controller 608 may be configured to determine the glucose concentration in the tear-film and the corresponding blood glucose concentration. In still another example, the reader 180 may determine the glucose concentration in the tear-film based on the sensor measurements and provide the tear-film glucose concentration to the sensor receiver 802 or the controller 608, which determines the corresponding blood glucose concentration. Thus, the functions of receiving the sensor measurements and determining the tear-film glucose concentration and the corresponding blood glucose concentration may be distributed between the reader 180, the sensor receiver 802, and the controller 608. In some examples, functionality of the sensor receiver 802 may be integrated into the controller 608.

Referring back to FIG. 7, at block 706, the method 700 includes obtaining a target glucose concentration. As described above with respect to FIG. 6, the controller 608 may be in communication with the set-point module 614 and/or the patient-specific information module 616. The controller 608 may be configured to receive from either module a target glucose concentration or a target range of glucose concentration (blood or tear-film) to be maintained in the patient 500 and is considered healthy for the patient 500. In some examples, the controller 608 may be configured to determine the target or the target range based on information provided by the set-point module 614 and/or the patient-specific information module 616. In examples, the target and/or the target range may be dynamic, i.e., changes over time based on other factors such as other health conditions or indicators in the blood or tear-film of the patient 500, time of day, meals consumed, or any other factor. In other examples, the target and/or the range may be fixed.

Referring back to FIG. 7, at block 708, the method 700 includes comparing the glucose concentration to the target glucose concentration. The controller 608 may be configured to compare the target and/or target glucose concentration with a current glucose concentration in the blood of the patient 500 determined at block 704. Accordingly, the controller 608 may be configured to determine an error or discrepancy between the target and/or target range of glucose concentration and the current glucose concentration.

Referring back to FIG. 7, at block 710, the method 700 includes based on the comparing, providing instructions to an insulin delivery device, where the instructions are configured to control an insulin delivery rate by the insulin delivery device. Based on the discrepancy between the target and/or target range of glucose concentration and the current glucose concentration, the controller 608 may be configured to provide instructions or commands (e.g., the commands 620 described at FIG. 6) to control the insulin delivery device 610. In an example, in addition to the comparing, the controller 608 may take into consideration diet and exercise information associated with the patient 500 in to determine a proper insulin amount or insulin delivery rate appropriate for the patient. The diet and exercise information may be provided to the controller 608 by the patient-specific information module 616 shown in FIG. 6, for example. The insulin delivery device 610 is shown mounted to an arm of the patient 500; however, the insulin delivery device 610 can be mounted in any other place (e.g., on a belt worn by the user) and is configured to inject insulin at a particular rate or dosage into a blood stream of the patient 500.

In an example, the controller 608 may provide the instructions such that the insulin delivery device 610 provides insulin at a rate that would cause the blood glucose concentration of the patient 500 to substantially meet the target glucose concentration. The blood glucose concentration substantially meets the target glucose concentration when the blood glucose concentration is within a predetermined threshold value from the target glucose concentration (e.g., within 2% from the target glucose concentration). For example, the insulin delivery device 610 may be configured, based on the instructions from the controller 608, to increase, decrease, or maintain the insulin delivery rate so as to cause the blood glucose concentration of the patient 500 to substantially meet the target glucose concentration.

In another example, the instructions may be configured to maintain a predetermined insulin delivery rate by insulin delivery device 610 when the glucose concentration is within the range. If the glucose concentration deviates from the range, the controller 608 may be configured to provide instructions such that the insulin delivery device 610 changes the insulin delivery rate to the blood stream 612 so as to bring the glucose concentration in the blood stream 612 within the range.

As shown in FIG. 8, the controller 608 is embedded within the display device 350. The display device may include a user interface 804. The user interface 804 may include a data input device and/or a data output device. The data output device may, for example, generate signals to initiate an alarm and/or include a display 806 for showing status of the controller 608 and/or a patient's vital indicators (e.g., blood glucose concentration over time). The data input device may include dials, buttons such as the button 808, pointing devices, manual switches, alphanumeric keys, a touch-sensitive display, combinations thereof, and/or the like for receiving patient and/or operator inputs. The data input device may be used for scheduling and/or initiating insulin bolus injections for meals, inputting patient-specific information, etc. Other input and output device are possible as well.

The display device 350 could be, for example, a wearable, laptop, desktop, handheld, or tablet computer, a mobile phone, a head-mounted display, or a subsystem of such a device. The display device 350 can include a processing system; e.g., a central processing unit (CPU), and a non-transitory computer readable medium configured to store at least program instructions that, when executed, perform functions of the user interface 804, the sensor receiver 802, and the controller 608. Although the controller 608 is depicted in FIG. 8 as embedded with the display device 350, the controller 608 could also be integrated into the insulin deliver device 610 or the reader 180, for example.

VIII. Conclusion

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

What is claimed is:

1. A system comprising:
    an eye-mountable device including a polymeric material;
    an electrochemical sensor mounted in the eye-mountable device, wherein the electrochemical sensor provides one or more sensor measurements indicative of glucose concentration in a tear-film contacting the eye-mountable device;
    a reader including one or more antennas, wherein the reader: (i) transmits radio frequency (RF) radiation to power the eye-mountable device and the electrochemical sensor, and (ii) receives indications of the one or more sensor measurements; and
    a controller in communication with the reader, wherein the controller: (i) receives information related to the one or more sensor measurements from the reader; (ii) obtains a target value for glucose concentration in the tear-film; (iii) compares the glucose concentration in the tear-film to the target value for glucose concentration in the tear-film; and (iv) based on the comparing, provides instructions to an insulin delivery device to control an insulin delivery rate to a blood stream by the insulin delivery device so as to reduce discrepancy between the glucose concentration in the tear-film and the target value for glucose concentration in the tear-film.

2. The system of claim 1, wherein the controller is integrated into: (i) the reader, (ii) the insulin delivery device, or (iii) a remote device in communication with the reader and the insulin delivery device.

3. The system of claim 1, wherein the eye-mountable device further includes a reagent that selectively reacts with an analyte in the tear-film contacting the eye-mountable device, and wherein the reagent is localized proximate the electrochemical sensor.

4. The system of claim 1, wherein the reader transmits the RF radiation to power the eye-mountable device and the electrochemical sensor at least a predetermined period of time before receiving the indications of the one or more sensor measurements.

5. The system of claim 1, wherein the polymeric material includes a channel configured to expose the electrochemical sensor to the tear-film contacting the polymeric material of the eye-mountable device.

6. The system of claim 1, wherein the controller establishes a rate of change of glucose concentration based on the information related to the one or more sensor measurements, wherein the instructions to the insulin delivery device are further based on the established rate of change of glucose concentration.

* * * * *